United States Patent
McKinnon et al.

(12)

(10) Patent No.: US 6,202,642 B1
(45) Date of Patent: Mar. 20, 2001

(54) ELECTRONIC MONITORING MEDICATION APPARATUS AND METHOD

(75) Inventors: Robert J. McKinnon, Highlands Ranch; Brian E. Dickerson; Thomas L. Taccini, both of Littleton, all of CO (US)

(73) Assignee: Medtrac Technologies, Inc., Lakewood, CO (US)

( * ) Notice: Subject to any disclaimer, the term of this patent is extended or adjusted under 35 U.S.C. 154(b) by 0 days.

(21) Appl. No.: 09/299,182

(22) Filed: Apr. 23, 1999

(51) Int. Cl.[7] .................................................. A61M 11/00
(52) U.S. Cl. .............................. 128/200.23; 128/200.16; 128/200.19; 128/204.23; 128/203.12; 128/205.23; 128/204.21; 128/200.14
(58) Field of Search .................. 128/200.23, 200.16, 128/200.19, 204.23, 203.12, 205.23, 204.21, 200.14

(56) References Cited

U.S. PATENT DOCUMENTS

| | | | |
|---|---|---|---|
| 5,363,842 | 11/1994 | Mishelevich et al. | 128/200.14 |
| 5,404,871 | 4/1995 | Goodman et al. | 128/200.14 |
| 5,520,166 | 5/1996 | Ritson et al. | 128/200.14 |
| 5,809,997 | * 9/1998 | Wolf | 128/200.23 |

FOREIGN PATENT DOCUMENTS

WO 99/35588   7/1999 (WO).

* cited by examiner

Primary Examiner—John G. Weiss
Assistant Examiner—Mital Patel
(74) Attorney, Agent, or Firm—Sheridan Ross P.C.

(57) ABSTRACT

A system for dispensing medication includes: a medicine canister that contains medicine to be dispensed, an actuator that houses the medicine canister and an adapter assembly that allows for obtaining information. The adapter assembly includes a connector assembly and an electronics module. The connector assembly connects to the medicine canister. The electronics module obtains information related to patient usage of medicine from the medicine canister. In another embodiment, a method for using the same electronics module with first and second medicine dispensing apparatuses, including a first medicine canister and a second medicine canister, is provided. The first medicine canister contains first medicine and the second medicine canister contains second medicine. First information, related to dispensing the first medicine, is stored with the electronics module joined to the first medicine dispensing apparatus. The electronics module is removed from the first medicine dispensing apparatus and joined to the second medicine dispensing apparatus. Second information, related to dispensing the second medicine, is also stored with the electronics module.

14 Claims, 17 Drawing Sheets

RxLog - Bradley Jackson

Device | Charts | Data | Patients | Notes

Patient Name Bradley Jackson
Patient ID jack
Serial No 0427002
Device ID

MDILog

Options
- ☑ Basic Functions
- ☑ Time Functions
- ☑ Device Messages
- ☑ Patient Info
- ☑ Audio On
- ☑ Spacer

MDILog Treatment

Medication: Serevent

Compliance Type: As Needed (PRN)

Dispenses Per Canister: 0000

Dosage
- Doses Per Day: 3
- Puffs Per Dose: 2
- Time Between: 04:00

Reminders
- #1 00:00
- #2 00:00
- #3 00:00
- #4 00:00
- #5 00:00

Device
- Dispense Events
- Memory Left
- Battery Voltage
- Battery Count

Treatment: Proventil - 2 Dispensed TID

FIG. 28

ELECTRONIC MONITORING MEDICATION APPARATUS AND METHOD

FIELD OF THE INVENTION

The present invention relates to prescribed medication monitoring, and in particular, to an apparatus and method related to a metered dose inhaler which includes an electronics module.

BACKGROUND OF THE INVENTION

Metered dose inhalers of various configurations are known for dispensing medication into the mouth of a patient. The medication is expelled from an actuator and inhaled by the patient, whereupon, the medication is absorbed in the mouth, throat and lungs. A medicine canister is inserted into the actuator so that the actuator may direct the flow of medication out a mouthpiece. The medicine canister is a small pressurized container with a nozzle. By pressing the nozzle, the contents of the canister are dispensed.

Some actuators have integral electronics which monitor various factors related to the dispensing of medication. The timing of the inhalation with respect to the dispensing of medication is important to assure delivery of the medication. The number of times medication is dispensed is also important to monitor. If the actuator is changed, however, the electronics integral to the actuator cannot be reused.

Actuators are standard components provided by many different manufacturers which have a variety of geometric configurations. For example, medicine canisters of different sizes require unique actuators. Further, some medicine manufacturers use proprietary actuators of unique configurations. Additionally, other factors dictate different configurations of actuators such that there is no standard actuator which can dispense all medications.

Applying a non-dedicated electronics module to a variety of actuators of different configurations is described in U.S. Pat. No. 5,809,997, which is assigned to the same assignee as the present application. With the electronics module adaptable to different actuators, this module can be reused, when a different actuator is utilized. In accordance with this previous design, to measure the timing of inhalation and use the non-dedicated electronics module, the actuator needs to be modified. A hole must be formed in the body of the actuator body to allow insertion of an air flow sensor in the path of the patient's inspiration and/or expiration. It would be advantageous to provide a combination of an electronics module and actuator hardware that further facilitates their use and interchangeability.

SUMMARY OF THE INVENTION

In accordance with the present invention, an apparatus and method related to a metered dose inhaler which includes an electronics module is disclosed. In one embodiment, a system for dispensing medication includes: a medicine canister that contains medicine to be dispensed, an actuator that houses the medicine canister and an adapter assembly that allows for obtaining information. The adapter assembly includes a connector assembly and an electronics module. The connector assembly connects to the medicine canister. The electronics module obtains information related to patient usage of medicine in the medicine canister.

In another embodiment, a method for using the same electronics module with two different medicine dispensing apparatuses is disclosed. A first medicine dispensing apparatus includes a first medicine canister which contains a first medicine. First information, related to dispensing the first medicine, is stored with an electronics module joined to the first medicine dispensing apparatus. A second medicine dispensing apparatus includes a second medicine canister containing a second medicine. The electronics module is removed from the first medicine dispensing apparatus and joined to the second medicine dispensing apparatus. Second information, related to dispensing the second medicine, is stored with the electronics module.

Based upon the foregoing summary, a number of important advantages of the present invention are readily discerned. A single electronics module may be reused even if the actuator changes. Additionally, no modifications are necessary to modify the actuator in order to connect the electronics module thereto.

Additional advantages of the present invention will become readily apparent from the following discussion, particularly when taken together with the accompanying drawings.

BRIEF DESCRIPTION OF THE DRAWINGS

FIG. 28 is a hard copy of display from a practitioner's software program which resides on a medical workstation;

DETAILED DESCRIPTION

Figure 2:
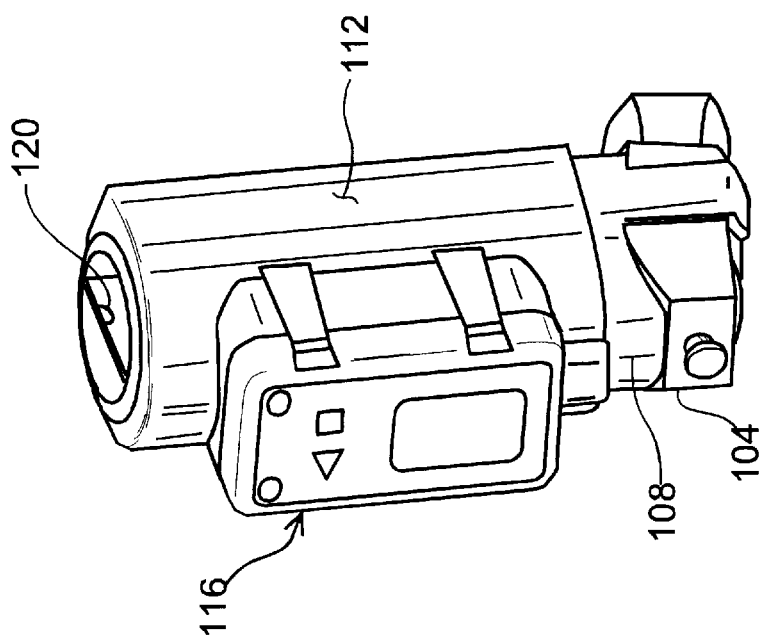
FIG. 2 is a back perspective view of an embodiment of the medicine dispensing system.
Figure 1:
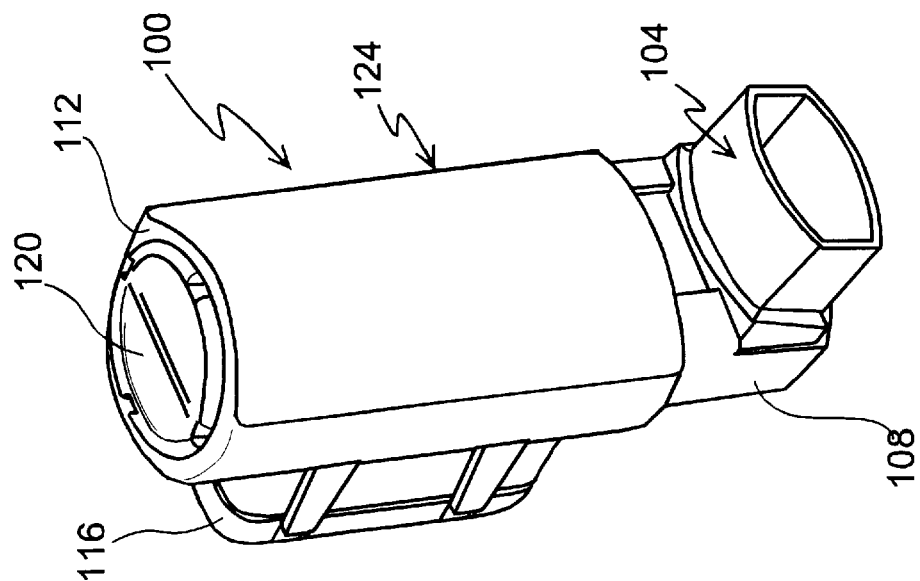
FIG. 1 is a front perspective view of an embodiment of the medicine dispensing system.

With reference to FIGS. 1 and 2, embodiments of the medicine dispensing system 100 are shown in front and back perspective views. The medicine dispensing system 100 includes an actuator 104, a heel adapter 108, a sleeve adapter 112, an electronics module 116, and a cap member 120. Included in a medicine dispensing apparatus 124 is the heel adapter 108, sleeve adapter 112, electronics module 116, and cap member 120. In other words, the medicine dispensing apparatus includes everything in the medicine dispensing system 100 except the canister 500, actuator 104 and electronics module 116. To allow monitoring the use of the medicine, the actuator 104 is modified by adding the heel adapter 108, sleeve adapter 112, electronics module 116, and cap member 120.

Figure 3:
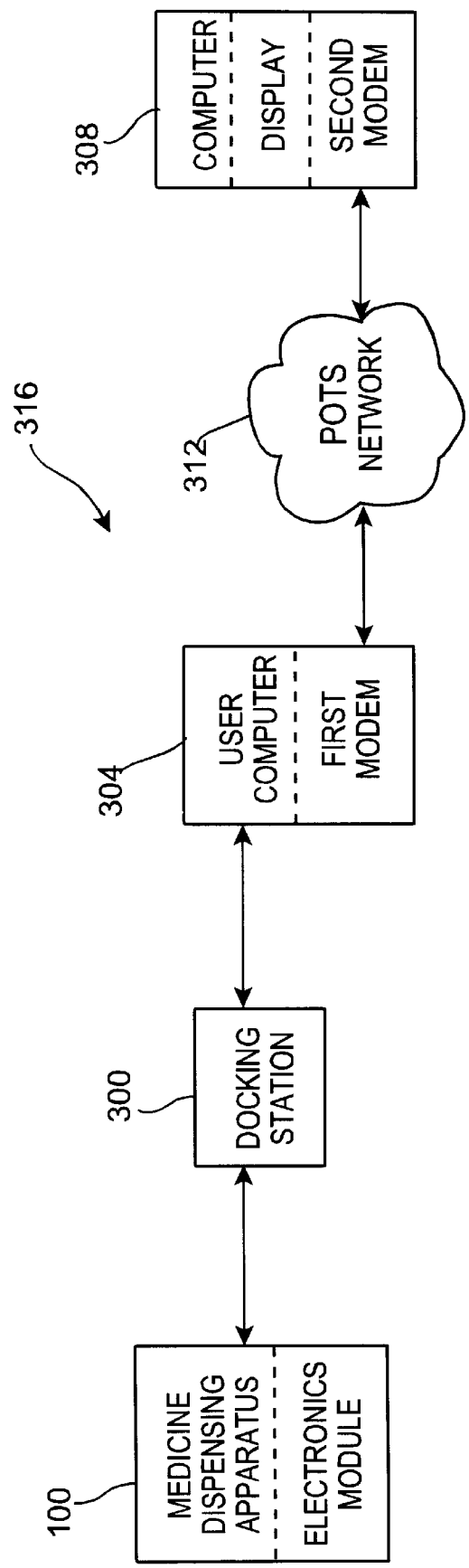
FIG. 3 is a block diagram illustrating an embodiment of a patient management system.

With reference to FIG. 3, a patient management system 316 is shown in block diagram form. The management system 316 includes the medicine dispensing system 100, a docking station 300, an user computer 304, and a medical workstation 308. When docked, the medicine dispensing system 100 communicates with the docking station 300 through wired or wireless methods. Preferably, infra-red (IR) transceivers are used to wirelessly communicate between the medicine dispensing system 100 and docking station 300. The docking station 300 is also coupled a user computer 304 which includes a first modem. Information is relayed between the first modem and a second modem in the medical workstation 308. The first and second modems may either directly connect through the plain old telephone system (POTS) network 312 or through a general purpose packet network, such as the Internet. Software on the medical workstation 308 communicates with software on the user machine 304 to allow programing of the medicine dispensing system 100 and retrieving data therefrom. The retrieval of data from the medical dispensing system 100 does not necessarily remove those data from -the medical dispensing system 100. However, commands from the medical workstation 308 can erase those data.

Figure 4:
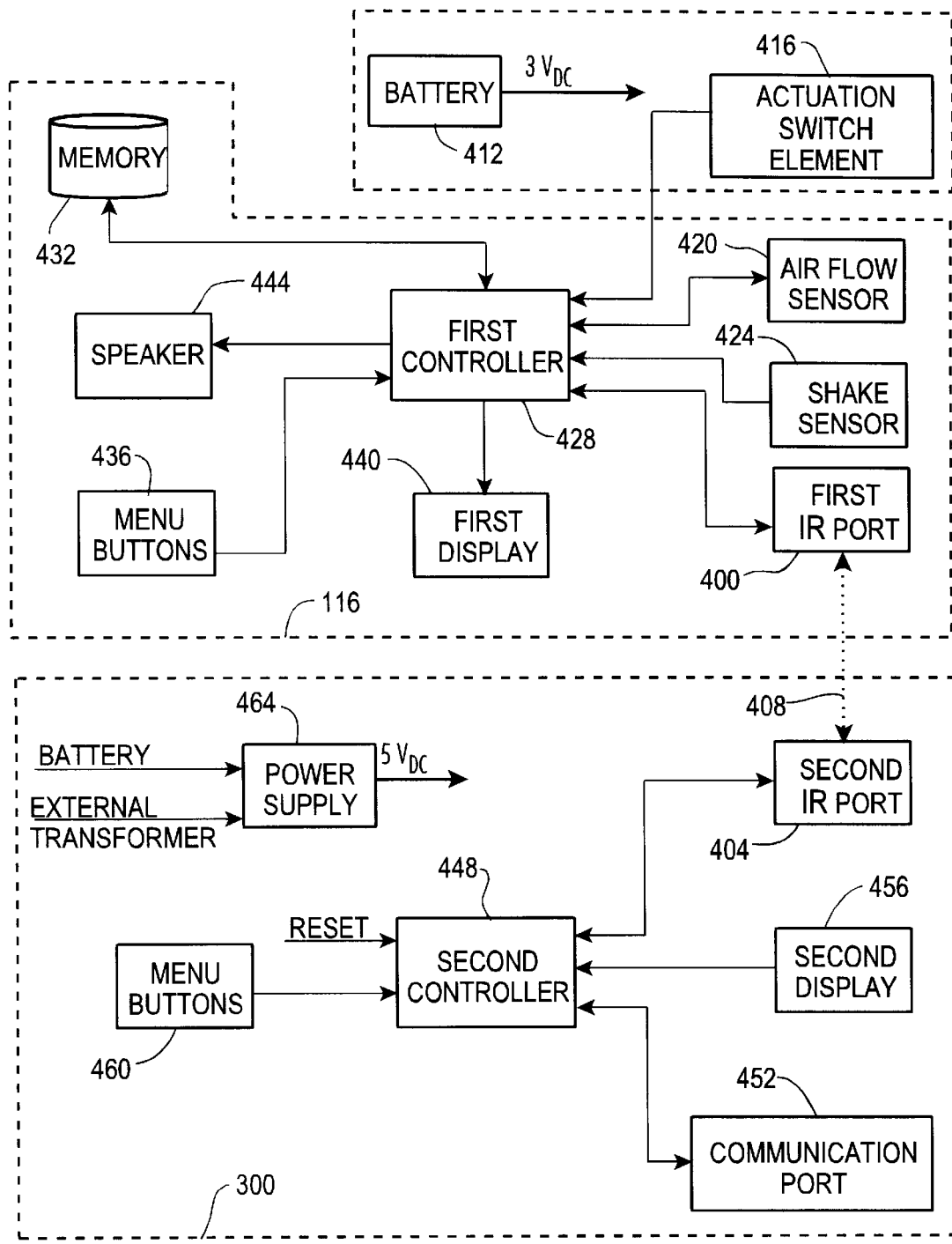
FIG. 4 is a block diagram depicting the medicine dispensing system and the docking station.

Referring next to FIG. 4, a block diagram of the electronics included in the medicine dispensing system 100 and docking station 300 are shown. A first IR transceiver port 400 communicates with a second IR transceiver port 404 by way of a wireless signal 408.

The format of the wireless signal 408 is bi-directional simplex transmission formatted as messages sent a byte at a time. Each message begins with a "wake-up" pulse of 20 $\mu$s, includes multiple message bytes and ends with an "end-of-message" pulse. Each message byte contains a start bit, 8 data bits and a stop bit. Bits are narrow 2 $\mu$s pulses which are separated from each other by 61 $\mu$s. The baud rate of the communication is 9,600.

The protocol of the wireless signal 408 is a master and slave protocol where the master initiates all communications by issuing commands, i.e., where the slave will not speak is until spoken to. Since this is a simplex protocol, the master must wait for a complete response from the slave before issuing the next command. The slave generally responds to the commands from the master within one second. If the checksum in the message is bad, the master will issue the command again. In this embodiment, the docking station 300 is the master and the medicine dispensing system 100 is the slave.

The general message protocol is one or more characters followed by a checksum and carriage return <CR>. All characters are encoded in ASCII format. Table I shows the commands for this protocol and Table II shows the data dictionary for the messages.

TABLE I

Command Definitions

| NAME | COMMAND | RESPONSE | PURPOSE |
| --- | --- | --- | --- |
| Battery Get | b<EM> | <BAT><EM> | To get current battery voltage and usage count since last changed. |
| Battery Clear | B0<EM> | <ACK> | To clear the battery usage count after installing a new battery. |
| Canister Get | c<EM> | <CAN><EM> | To get the current canister usage remaining count. |
| Canister set | C<CAN> | <ACK> | To preset the correct number of doses available in the canister for the current medication. |
| Get Record N | d<RECNO> | <RECNO><RECORD><EM> | To get a data log record |
| Set Record N | D<RECNO><RECORD> | <ACK> | Generate a test data record utilizing input record for data. |
| Header Set | H<HEADER> | <ACK> | Set header which is a text field to be used by the display |

TABLE I-continued

Command Definitions

| NAME | COMMAND | RESPONSE | PURPOSE |
|---|---|---|---|
| | | | software as desired. |
| Header Get | h<EM> | <HEADER><EM> | Get header which is a text field to be used by the display sofware as desired. |
| Product ID Get | i<EM> | <ID><FIRM><EM> | Get product id string with model and serial number and software revision (from ROM). |
| Product ID Set | I0<ID> | <ACK> | Set product id string with model and serial number. Needs 0 to validate the command. Note firmware <FIRM> is not set with this command. |
| Canister Reset | K<EM> | <ACK> | Initiate canister replacement re-setting counts. |
| Calibration Set | LO<HRES><VOLT> | <ACK> | Set inhalation threshold and new battery voltage baseline. |
| Calibration Get | l<EM> | <THRESHOLD><VOLTAGE><EM> | Get inhalation threshold and new battery voltage baseline settings. |
| Medication Set | M<MEDNAME> | <ACK> | Set patient medication text for display and number for flow calibration. |
| Medication Get | m<EM> | <MEDNAME><EM> | Get patient medication text for display and number for flow calibration. |
| Options Set | O<OPTIONS> | <ACK> | Set training and display options according to <options> definition. Generally used for display and alarm control. |
| Options Get | o<EM> | <OPTIONS><EM> | Get training and display options according to <options> definition. Generally used for display and alarm control. |
| Patient Set | P<NAME><EM> | <ACK> | Set patient name text for display. |
| Patient Get | p<EM> | <NAME><EM> | Get patient name text. |
| Reminder Set | R<REMINDERS> | <ACK> | Set reminders for usage and docking. |
| Reminder Get | r<EM> | <REMINDERS><EM> | Get current reminders. |
| Status | s<EM> | <DEVTYPE><STATUS><EM> | Provide a handshake and to provide the interpreter or application program with device battery level data information on operational errors encountered since last query. |
| Time Set | T<YR><DATE/TIME><EM> | <ACK> | Set GMT time/date and time zone of device relative to GMT. |
| Time Get | t<EM> | <YR><DATE/TIME><EM> | Get GMT time/date and time zone of device relative to GMT |
| Get Usage Count | u<EM> | <USE><EM> | Get usage count since last clearing of log. |
| Set Usage Count | U0<EM> | <ACK> | Clear usage count and data log. 0 is utilized as verification of command. |
| Variable Set | V<VN><HEADER> | <ACK> | Set header number N which is a text field to be used by the display software as desired. |
| Variable Get | v<VN><EM> | <HEADER><EM> | Get header number N which is a text field to be used by the display software as desired. |

TABLE II

Data Dictionary

| FIELD | DETAIL | EXPLANATION |
|---|---|---|
| <ACK> | <CR> or<br><ERR><CR> | no error response<br>error response |
| <BAT> | VVUUUU | VV: 2 character voltage range 0.0–3.5.<br>UUUU: 4 character usage count. |
| <CAN> | NNNN | 4 digit count of current canister contents. |

TABLE II-continued

Data Dictionary

| FIELD | DETAIL | EXPLANATION |
|---|---|---|
| <DATA> | <XX> | 2 digits hexadecimal event data |
| | Bit. # | Desc. |
| | 7 | Test event |
| | 6 | medication dispensed |
| | 5 | inhale true |
| | 4 | shake true |
| | 3 | multiple dose |
| | 2 | late inhale |
| | 1,0 | # tics to inhale |
| <DATE/TIME> | MMDDHHMMSS | Date/time format |
| <DEVTYPE> | C | Indicates Device Type |
| <DISPSTAT> | <XX> | 2 digits hexadecimal internal Electronics |
| | Bit. # | Module status |
| | 7 | Desc. |
| | 6 | disable logging |
| | 5 | inhale delay warm-up |
| | 4 | inhale delay |
| | 3 | dispense check in-process |
| | 2 | arm check |
| | 1 | inhale check in process |
| | 0 | armed |
| <EM> | <optional checksum><CR> | end of message |
| <ERR> | 0 | no error same as only <CR> |
| | 1 | not understood |
| | 2 | checksum error |
| | 3 | format error |
| <FIRM> | C4 | 4 character Firmware revision from Processor ROM i.e. 0F00 |
| | | Byte 1 is a variation code |
| | | Byte 2 is Firmware revision |
| | | Bytes 3–4 intermediate engineering release # |
| <HEADER> | <C28> | 28 character display program specific info. |
| <ID> | <C12> | 12 character product id and serial number "rr" is the circuit board assembly revision number, "bbbb" is the four digit circuit board batch number, "§" is the circuit board assembly serial number. |
| <MDISTAT> | <XX> | 2 digits hexadecimal internal electronics |
| | Big. # | module status |
| | 7 | Desc. |
| | 6 | Time to Log |
| | 5 | shake |
| | 4 | inhale correct |
| | 3 | inhaled late |
| | 2 | medication delivery |
| | 1 | multiple |
| | 0 | advance reminder time |
| <MDISTAT_E> | <XX> | 2 digits hexadecimal internal electronics |
| | Bit. # | module status |
| | 7 | Desc. |
| | 6 | no start bit |
| | 5 | log full |
| | 4 | QC time |
| | 3 | battery low |
| | 2 | canister empty |
| | 1 | beep high |
| | 0 | menus enabled diagnostic mode |
| <MEDNAME> | <C16> | 16 character name |
| <NAME> | <C16> | 16 character name |
| <OPTIONS> | <XX> | 2 digits hexadecimal mask |
| | Bit. # | Feature. |
| | 0 | Display level 0 Basic |
| | 1 | Display level 1 Enhanced Time/Canister |
| | 2 | Display level 2 patient info submenu |
| | 3 | Display level 3 device info submenu |
| | 4 | Patient info feedback |
| | 5 | Audible reminders |
| | 6,7 | 00 - Standard MDT |
| | | 10 - Autohaler logic |
| | | 11 - Non MDI device no inhale test |
| | | NOTE: Level 1 must include level 0 |
| | | Level 2 must include level 0 |

TABLE II-continued

Data Dictionary

| FIELD | DETAIL | EXPLANATION |
|---|---|---|
| <RANGE> | <BBBBEEEE> | BBBB: 4 digit hex begin address |
| | | EEEE: 4 digit hex ending address |
| <RECNO> | NNNN | 4 digit decimal record number |
| <RECORD> | <DATE/TIME><DATA> | Month/day etc. |
| | | Data record |
| <REMINDERS> | <HHMMHHMMHHMM | HH: 2 digit hour |
| | HHMMHHMMHHMM> | MM: 2 digit minute of hour |
| | | item 1–5 dose reminders |
| | | item 6 docking reminder |
| | | Unset alarms must be set to 9999 as 0000 is |
| | | midnight in 24 hour format. |
| <STATUS> | <MDISTAT><MDISTAT_E><DTSP_STAT> | |
| | <NOTDEFINED><NOTDEFINED><NOTDEFINED><NOTDEFINED> | |
| <USE> | NNNNLLLL | NNNN: 4 digit count number of uses |
| | | LLLL: 4 digit count of uses available (left in |
| | | memory) |
| <VN> | N | Single digit variable number |
| <YR> | YY | 2 digit year |

In this embodiment, the electronics in the medicine dispensing apparatus 100 are divided between the sleeve adapter 112 and the electronics module 116. The sleeve adapter 112 houses a battery 412 (for example, a 3 $V_{DC}$ coin-shaped battery) and an actuation switch element 416. The electronics module 116 includes the first IR port 400, an air flow sensor 420, a shake sensor 424, a first controller 428, memory 432, menu buttons 436, a first display 440, and a speaker 444.

The first controller 428 manages the operation of the electronics through embedded software or firmware. The time and date of activation of the actuator 104 is recorded in the memory 432. The memory 432 may be volatile or non-volatile and may serve as the exclusive storage device or be supplemented by other memory in the first controller 428. In this embodiment, the memory 432 is 4 Kbytes and stores 1,320 actuation events.

The actuation switch element 416 detects dispensing of medication. During use, the mouth of the actuator is placed in the mouth of the patient, whereafter, the sleeve adapter 112 is pressed toward the mouthpiece to activate a dispensing valve in the medicine canister. When the sleeve adapter 112 is pressed, the actuation switch element 416 integral to the sleeve adapter 112 detects the dispensing of medication. The time of dispensing is recorded by the first controller 428. The actuation switch element 416 has a spring member which completes a circuit when the sleeve adapter 112 slides toward the heel adapter 108 so that dispensing may be recorded. In this embodiment, up to two dispensing per second can be recorded in this way.

The air flow sensor 420 measures the inspiration which pulls the medication aerosol into the mouth of the patient. In this embodiment, a heated thermistor is used to measure air flow. The heated thermistor in the air flow sensor 420 is cooled by the air flow. The time and amount of cooling may be measured and recorded by the first controller 428. To conserve memory space, a flag may be used to indicate the presence of sufficient inspiration proximate in time to the dispensing of medication instead of recording time and amount. Fifteen liters per minute of inhalation or more can be detected with this sensor.

Shaking of the medicine dispensing apparatus 100 is recorded by the shake sensor 424. Prior to dispensing, shaking of the medicine canister mixes the contents to assure efficacy of some medications. In one embodiment, the shake sensor 424 includes a sliding magnet which moves when the medicine dispensing apparatus 100 is shaken to produce a signal indicative of the movement. Other types of sensors, such as accelerometers, could also be used to record the shaking. To record this event, a flag is stored which indicates a successful shaking before dispensing medication. Shaking which is not followed by actuation of the dispenser 100, is not recorded to conserve memory.

The first display 440 provides status information and prompts to the patient. In one embodiment, the display is a liquid crystal display (LCD) with two lines where each has eight characters. The first display 440 provides information such as the patient's name, medication name, dose count, current time and date, number of remaining doses, time of last use, time of next use, low medication reminder, low battery reminder, battery level, device identifier or serial number, and memory capacity remaining. Menu buttons 436 allow scrolling through menu options and selecting features. In this embodiment, the menu buttons 436 are membrane switches.

A speaker 444 is provided to allow auditory feedback from the electronics module 116. The speaker 444 could produce an alarm when a dose of medication were required. Other interactions between the patient and electronics module 116 could be enhanced with auditory feedback from the speaker 444.

The docking station 300 serves as a conduit of the medical workstation 308. Once the medication delivery system 100 is placed in the docking station 300, the data stored in memory is retrieved and any programming or reprogramming of the medication delivery system 100 takes place. Programming is needed for a newly issued electronics module 116 and reprogramming is required when the electronics module 116 is attached to a different actuator 104. The docking station 300 includes the second IR port 404, a second controller 448, a communication port 452, a second display 456, menu buttons 460, and a power supply 464. The second IR port 404 communicates with the first IR port 400 when the medicine dispensing system 100 is docked by way of the wireless signal 408.

The operation of the docking station is managed by the second controller 448. Firmware in the controller 448 receives and processes information from the communication port 452, second IR port 404 and menu buttons 460. Additionally, output for the display 456, second IR port 404 and communication port 452 is prepared by the controller 448.

The communication port 452 provides a conduit to the user computer 304 and, ultimately, the medical workstation 308. In one embodiment, the communication port 452 is a standard serial port (i.e., RS-232) commonly found on computers. Software on the user machine 304 allows interaction with the communication port 452 so that programming information and data may pass therethrough.

The docking station 300 also contains a second display 456 and menu buttons 460. The second display 456 could be a LCD, or other type of display. Status information and user prompts could be displayed to assist the patient. For example, error messages could be displayed instructing the patient to reseat the medicine dispensing system 100 in order to allow for better IR communication. The menu buttons 460 allow interaction between the docking station 300 and patient. In one embodiment, the menu buttons 460 are membrane switches.

Power is supplied to the docking station 300 from a power supply 464. Either an external transformer or internal batteries provide energy to the power supply 464. Further conditioning of these two power sources is provided by the power supply 464 to produce, for example, 5 $V_{DC}$ for the circuitry within the docking station 300.

Figure 5:
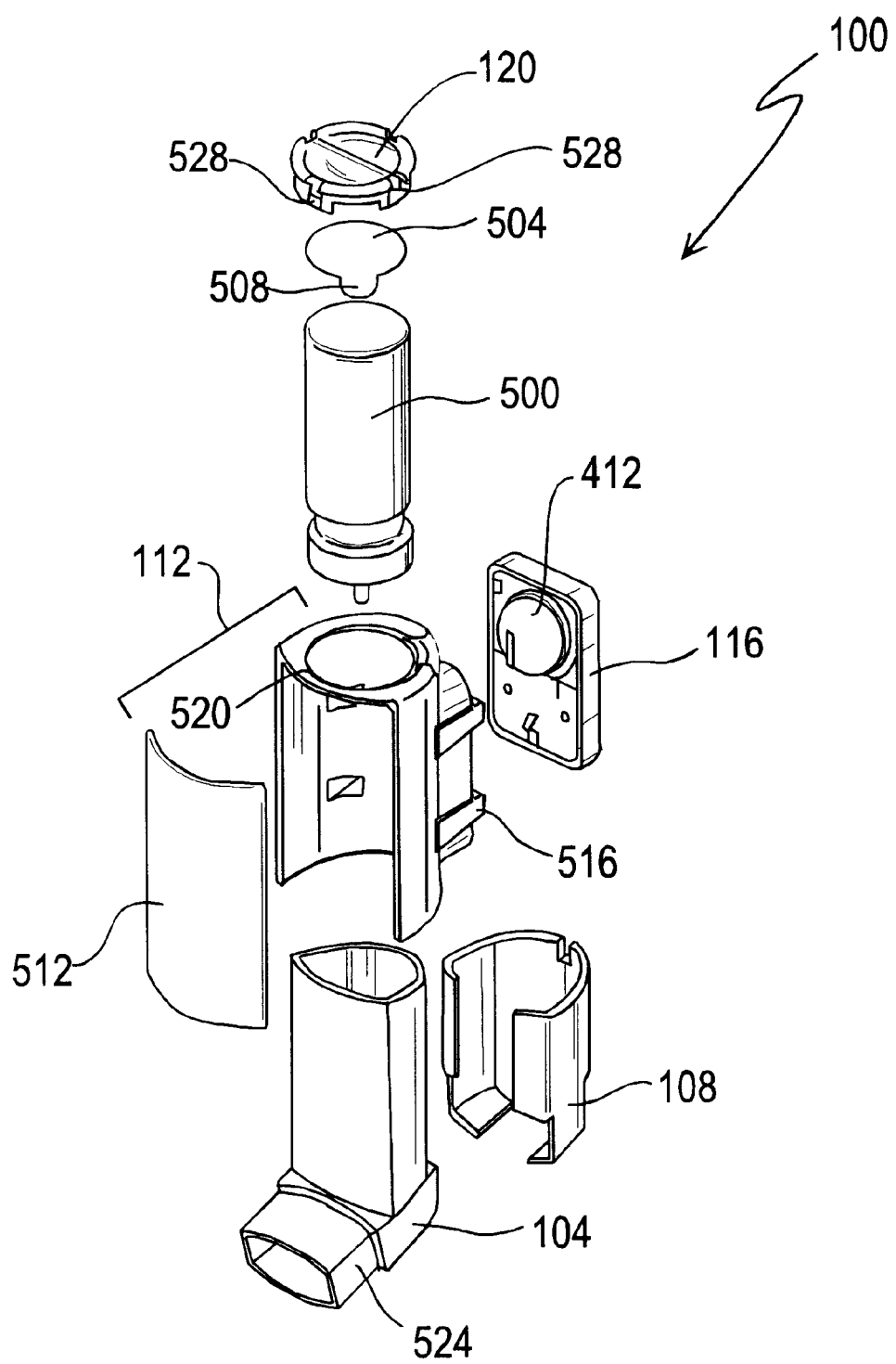
FIG. 5 is an exploded perspective view of one embodiment of the medicine dispensing system.

With reference to FIG. 5, an exploded view of the medicine dispensing system 100 is shown. Included in the medicine dispensing apparatus 100 is a connector assembly, the electronics module 116, the medicine canister 500, and the actuator 104. The connector assembly includes the cap member 120, a double-sided tape 504, the sleeve adapter 112, and the heel adapter 108. The cap member 120, double-sided tape 504, and sleeve adapter 112 move with the medicine canister 500 to dispense the medicine through a mouthpiece 524. In this embodiment, the cap member 120, sleeve adapter 112 and heel adapter 108 are made of molded plastic.

The cap member 120 is attached to the canister 500 with a double-sided tape 504. The cap member 120 has the double-sided tape 504 pre-attached. A liner covers the side of the tape 504 which will eventually attach to the canister 500. A release tab 508 is included in the double-sided tape 504 which eases removal of the liner to expose the adhesive tape 504 beneath. Upon removal of the liner, the canister 500 is pressed against the double-sided tape 504 to affix the cap member 120 to the canister 500. Once the double-sided tape 504 is affixed between the cap member 120 and medicine canister 500, the whole assembly may be slid into an opening 520 in the sleeve adapter 112. Snaps 528 around the periphery of the cap member 120 snap into the sleeve adapter 112 to affix the two together. In other embodiments however, the cap member 120 could screw into the sleeve adapter 112 to interconnect the two.

The sleeve adapter 112 has a window 512 for viewing a medication label and connectors 516 for attaching the electronics module 116. The window 512, integral to the sleeve adapter 112, allows reading any prescription information on the medicine canister 500 by rotating the cap member 120. The electronics module 116, in this embodiment, also includes the actuation switch element 416 and battery 412. The connectors 516 removably attach the electronics module to the sleeve adapter 112. A tool such as a flat-head screw driver can be used to pry the connectors 516 away from the electronics module 116. When the battery 412 is depleted in one embodiment, the battery 412 and all other components, except for the electronics module 116, are replaced since such components are disposable and for sanitary reasons this is preferred. In another embodiment, the battery only could be replaced when its charge is depleted and is not rechargeable.

The heel adapter 108 is attached to the body of the actuator 104. Snaps on the heel adapter 108 attach around the back and bottom of the actuator 104. After installation of the heel adapter 108, a mouthpiece of the actuator is not obstructed in any way. In this embodiment, no modification of the actuator is necessary for attaching the heel adapter 108 and sleeve adapter 112. The heel adapter 108 guides the sleeve adapter 112 and provides a back-stop for the spring member which senses actuation of the medicine dispensing system 100.

Figure 6:
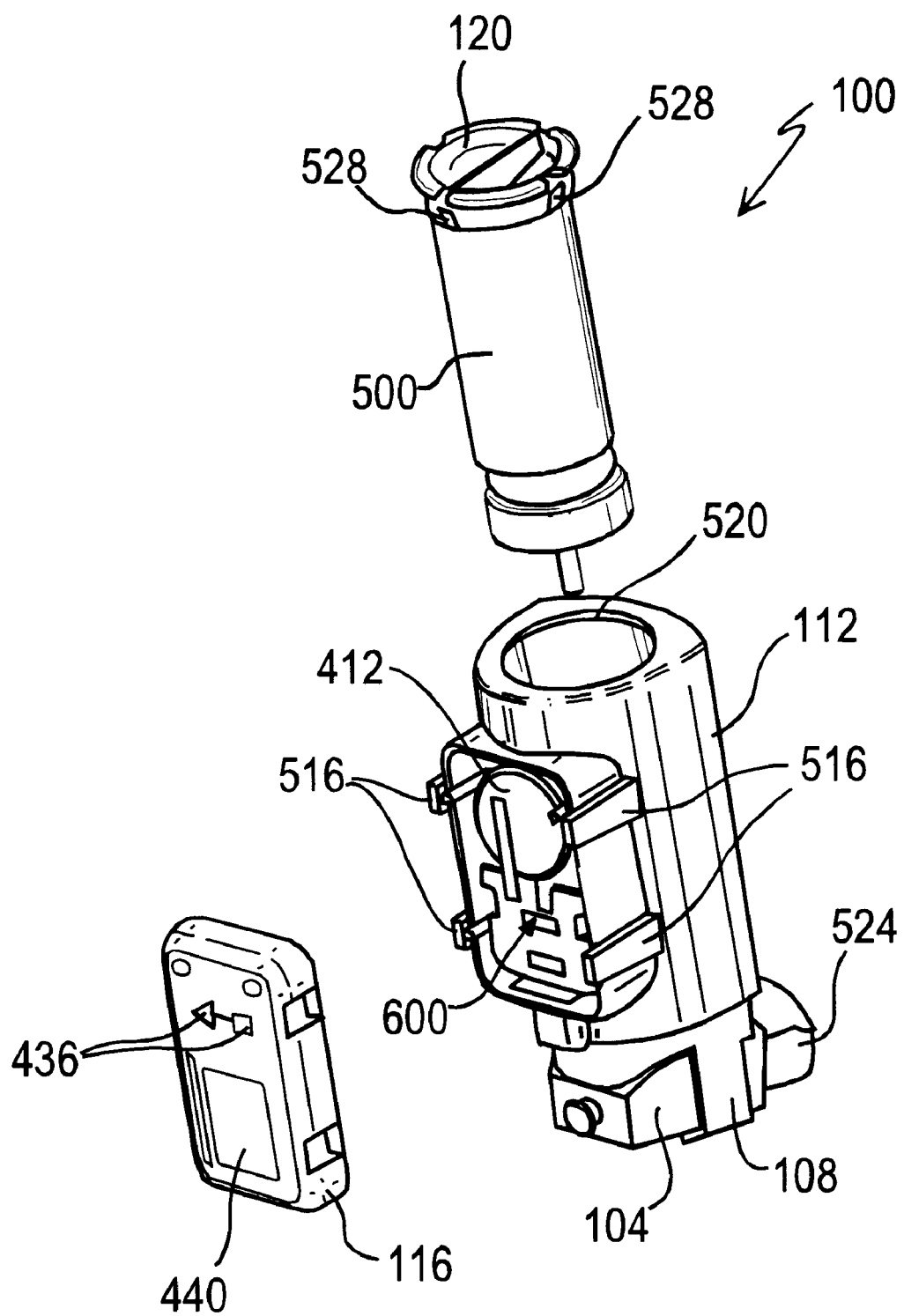
FIG. 6 is a partially exploded view of an embodiment of the medicine dispensing system.
Figure 10:
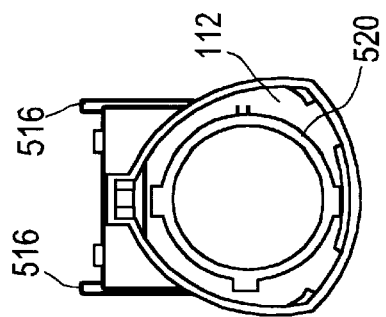
FIG. 10 is a top plan view of the sleeve adapter of FIG. 7.
Figure 9:
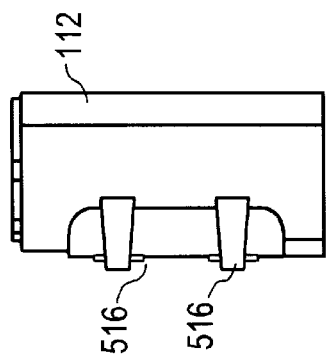
FIG. 9 is a side elevational view of the sleeve adapter of FIG. 7.
Figure 8:
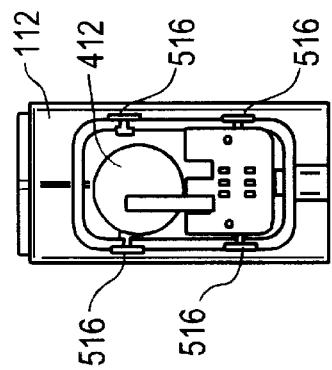
FIG. 8 is a back elevational view of the sleeve adapter of FIG. 7.
Figure 7:
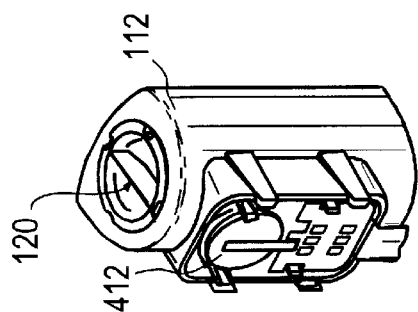
FIG. 7 is a perspective view of the sleeve adapter portion of the medicine dispensing apparatus.
Figure 14:
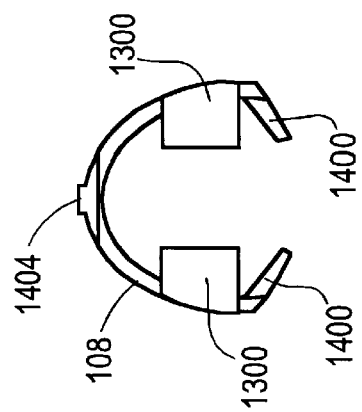
FIG. 14 is a top plan view of the heel adapter of FIG. 11.
Figure 13:
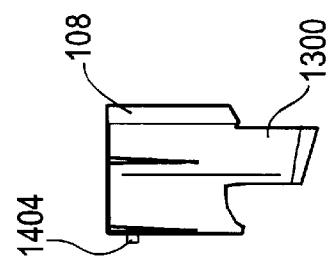
FIG. 13 is a side elevational view of the heel adapter of FIG. 11.
Figure 12:
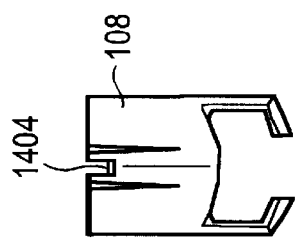
FIG. 12 is a back elevational view of the heel adapter of FIG. 11.
Figure 11:
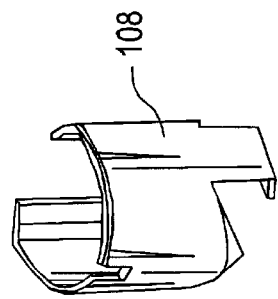
FIG. 11 is a back perspective view of a heel adapter portion of the medicine dispensing apparatus.

With reference to FIG. 6, an embodiment of the medicine dispensing system 100 is shown in an exploded view. The medicine canister 500 is engaged with the cap member 120. In this embodiment, the battery 412 and actuation switch element 416 are integral to the sleeve adapter 112. Electrical contacts 600 allow coupling the battery 412 and spring member to the electronics module 116. The menu buttons 436 and the first display 440 are shown on the electronics module 116.

Referring to FIGS. 7–10, the sleeve adapter 112 is respectively shown in perspective, back, side and top views. The cap member 120 is shown attached to the sleeve adapter 112. In this embodiment, the battery 412 and actuation switch element 416 are integral to the sleeve adapter 112. When the battery 412 expires, the whole sleeve adapter 112 is removed and replaced, and it is recommended, everything but the electronics module 116 also be replaced. The sleeve adapter surrounds at least a majority of a perimeter of the actuator.

With reference to FIGS. 11–14, the heel adapter 108 is respectively shown in perspective, back, side and top views. Included in the heel adapter 108 are vertical connectors 1300, horizontal connectors 1400 and a switch engaging member 1404. The vertical connectors 1300 wrap around the bottom of the actuator 104 and the horizontal connectors 1400 wrap around the front of the actuator 104. When the sleeve adapter 112 is compressed to dispense medication, the switch engaging member 1404 presses against the spring member to close the actuation switch 416. In this way, the dispensing of medication is recorded. The sleeve adapter 124 snaps together with the heel adapter 108.

Figure 17:
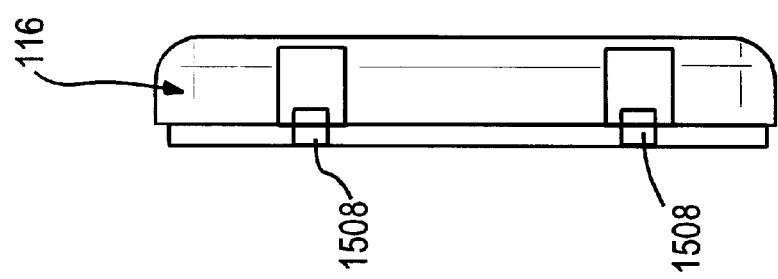
FIG. 17 is a side elevational view of the electronics module of FIG. 15.
Figure 16:
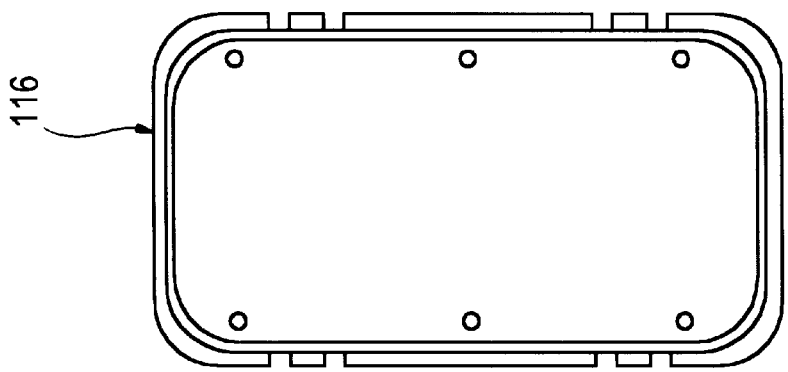
FIG. 16 is a front elevational view of the electronics module of FIG. 15.
Figure 15:
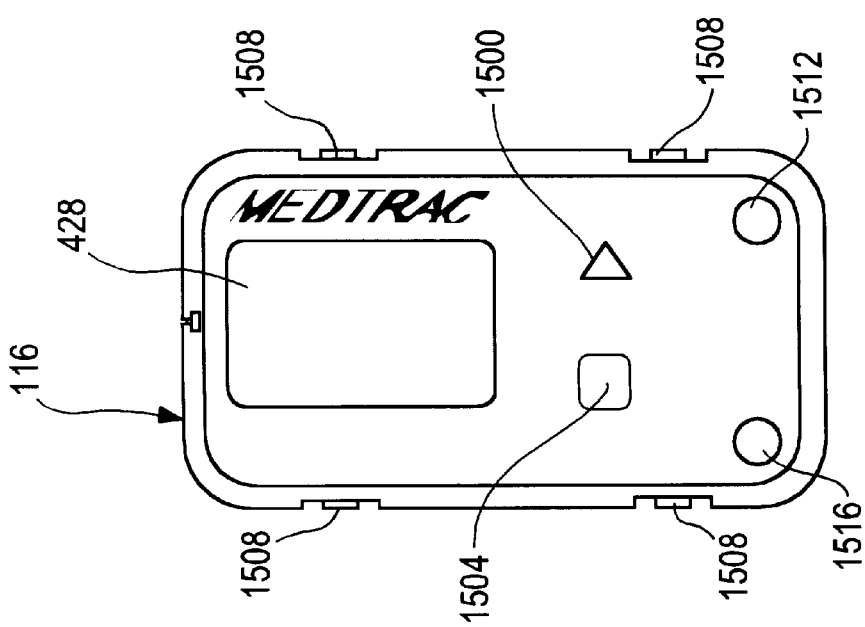
FIG. 15 is a back elevational view of an electronics module of the medicine dispensing system.

Referring next to FIGS. 15–17, an embodiment of the electronics module 116 is respectfully shown in backs front and side views. A scroll button 1500 and a select button 1504 comprise the two menu buttons 436. The scroll button 1500 allows cycling through the various menus and options and the select button 1504 allows selection of those options. To allow the IR communication of the first IR port 400, an IR transmitter and receiver 1512, 1516 are provided. When docked, the IR elements 1512, 1516 face a conjugate pair of IR elements to allow communication. Latches 1508 are provided which mate with connectors 516 on the sleeve adapter 122. The latches allow removably attaching the electronics module 116 to the sleeve adapter 122. Although not shown in FIG. 16, the front of the electronics module 116 includes connectors which mate to the electrical contacts 600 on the battery and actuation switch element subassembly. Removal of the electronics module 116 renders portions of the medicine dispensing system 100 functionally inoperable.

Figure 18:
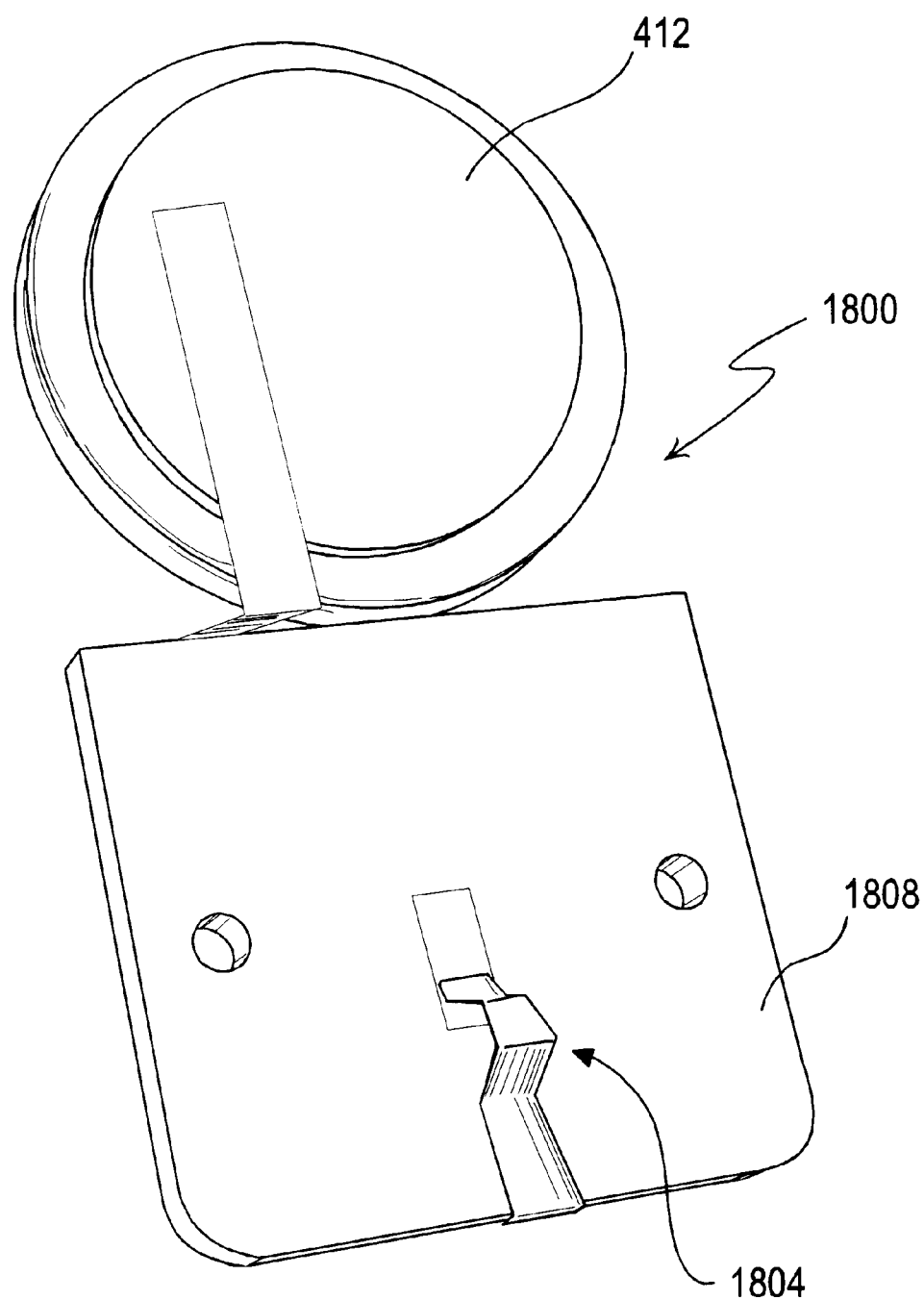
FIG. 18 is a front perspective view of the battery and actuation switch element subassembly.

With reference to FIG. 18, a perspective view of a battery and actuation switch element assembly 1800 is shown. In this embodiment, the battery and actuation switch element assembly 1800 is installed integrally to the sleeve adapter 112. The battery and actuation switch element assembly 1800 includes a spring member 1804, a circuit board 1808, and the battery 412. Electrical contacts 600, on the side of the circuit board 1808 away from the spring member 1804, couple the battery and actuation switch element assembly 1800 to the electronics module 116. When the sleeve adapter 112 is pressed toward the heel adapter 108, the spring member 1804 is temporarily bent by the switch engaging member 1404 to complete an electrical loop. In this way, dispensing of the medication is detected.

Figure 19:
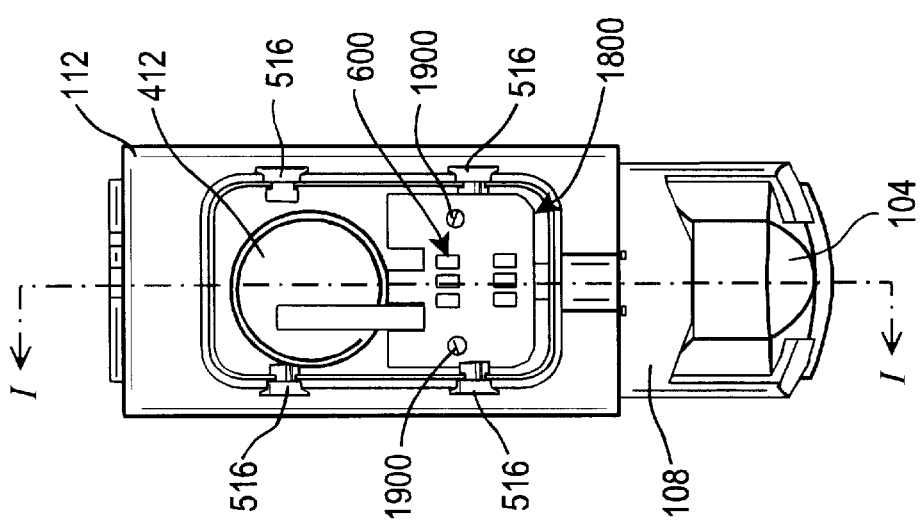
FIG. 19 is a back elevational view of the medicine dispensing apparatus.

Referring to FIG. 19, a back view of the medicine dispensing apparatus is shown. The battery and actuation switch element assembly 1800 is shown installed in the sleeve adapter 112. In one embodiment, two fasteners 1900 are threaded through the circuit board 1808 to affix the battery and actuation switch element assembly 1800. Alternatively, the circuit board 1808 could be ultrasonically staked to the sleeve adapter 112. It is noted, other embodiments integrate the battery and actuation switch element assembly 1800 into the electronics module 116.

Figure 20:
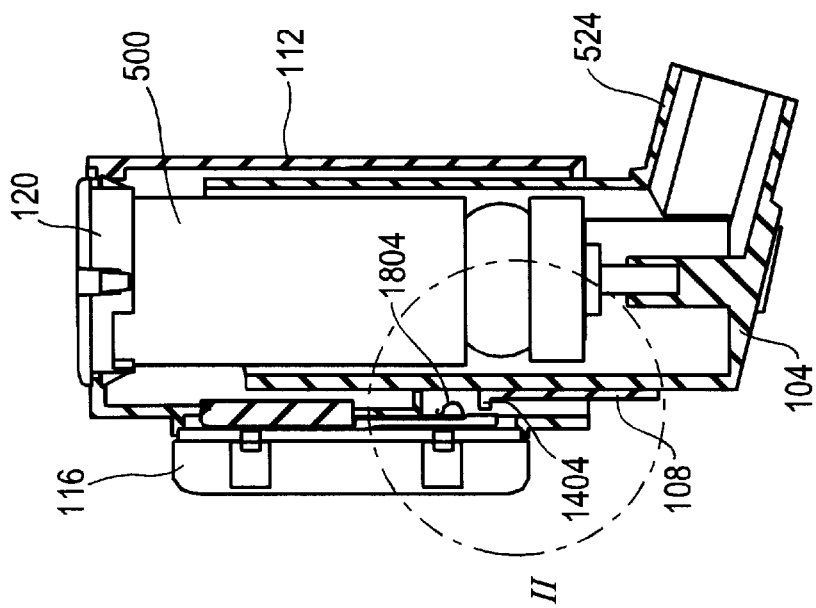
FIG. 20 is a side sectional view along the I—I cross section of FIG. 19 which also includes the electronics module.
Figure 22:
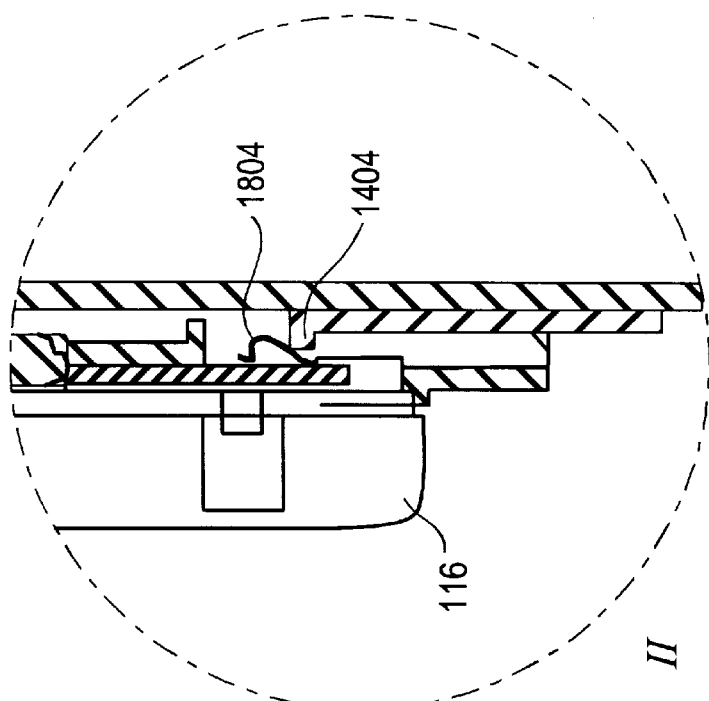
FIG. 22 is the enlarged portion II of FIG. 20 which shows the spring member activated.
Figure 21:
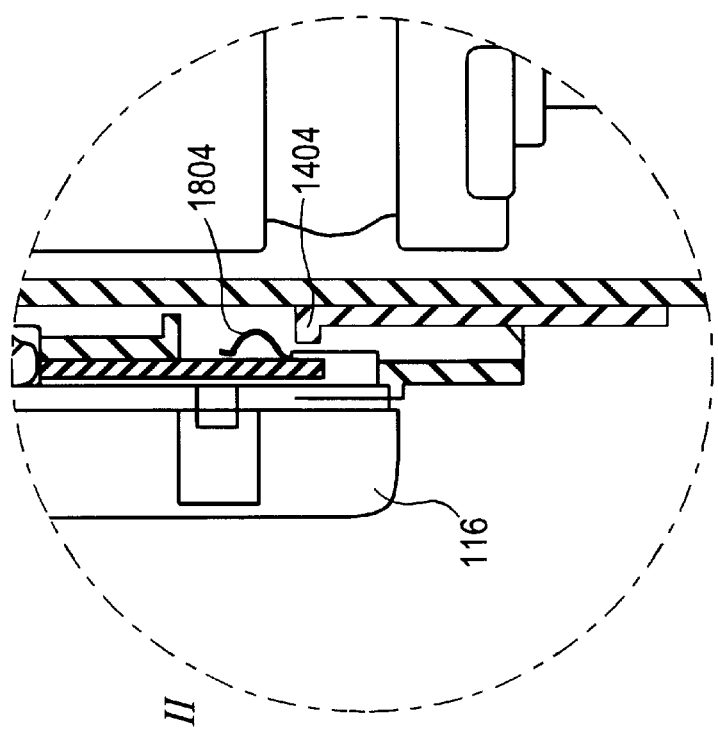
FIG. 21 is an enlarged portion II of FIG. 20 which shows the spring member deactivated.
Figure 23:
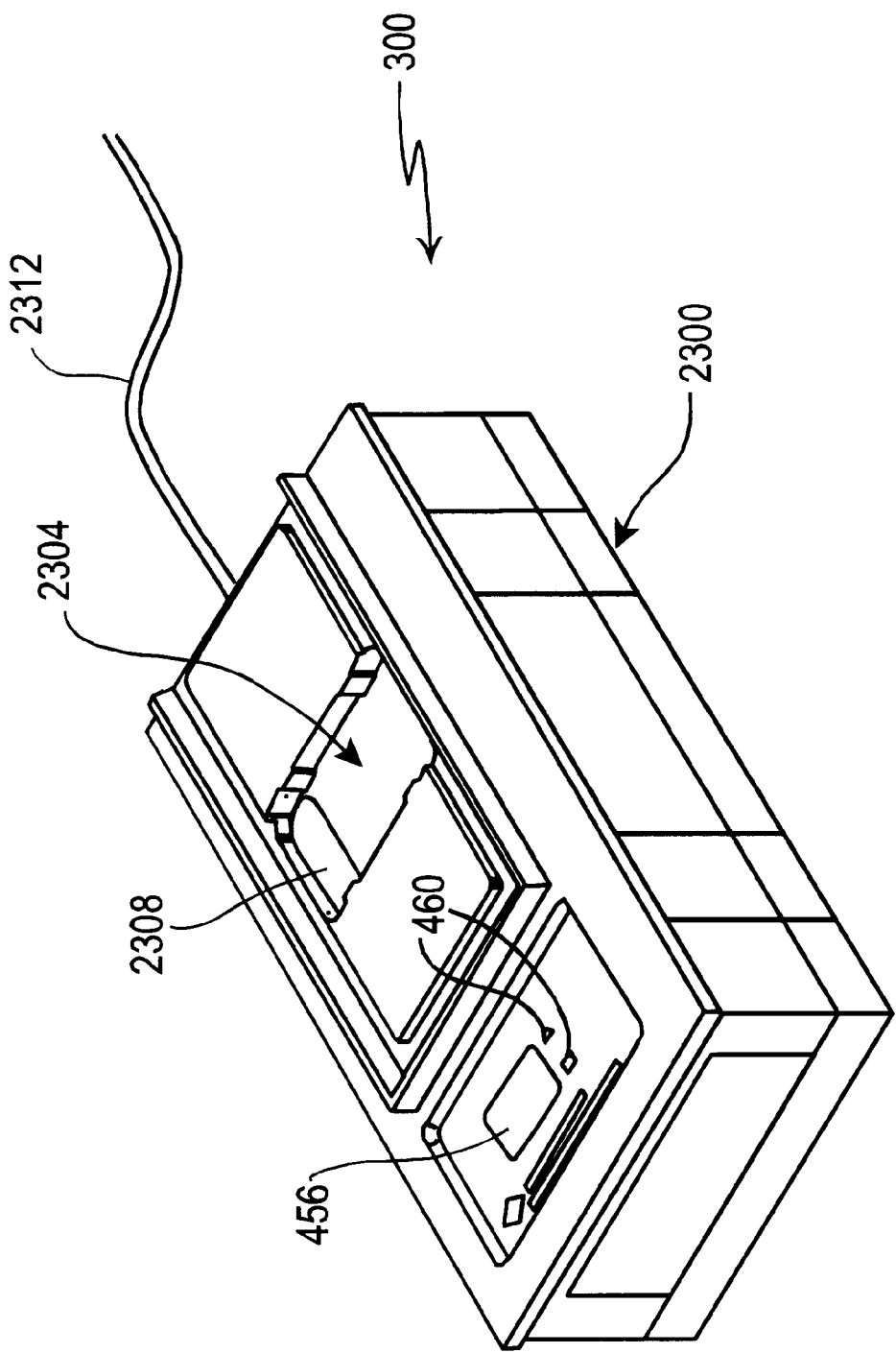
FIG. 23 is a perspective view of the docking station for the medicine dispensing system.
Figure 25:
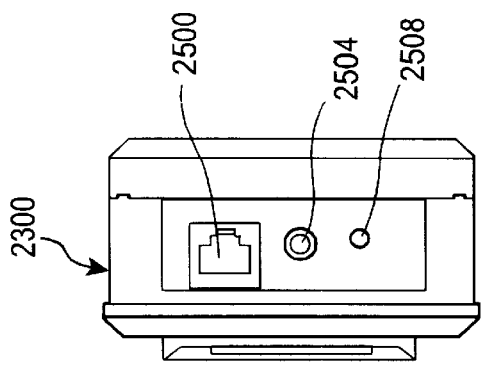
FIG. 25 is a back elevational view of the docking station of FIG. 23.
Figure 24:
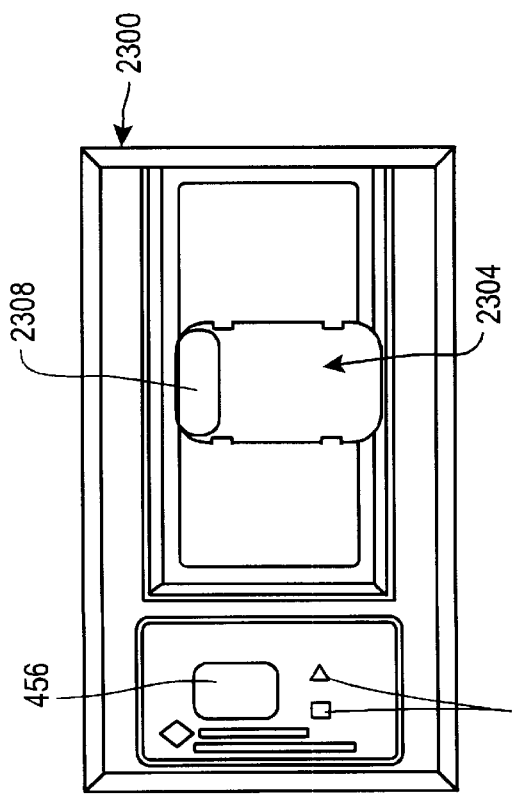
FIG. 24 is a top plan view of the docking station of FIG. 23.
Figure 26:
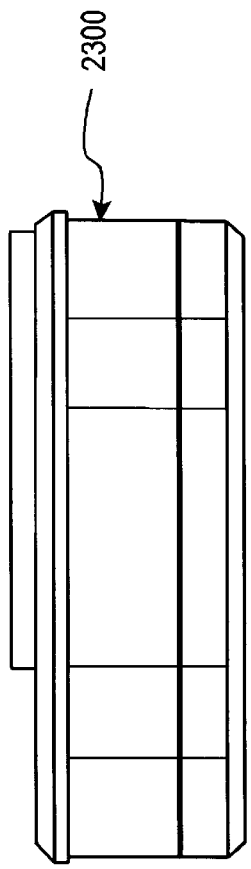
FIG. 26 is a side elevational view of the docking station of FIG. 23.

FIGS. 20–22 detail the operation of the actuation switch element 416. FIG. 20 shows a side sectional view along the I—I cross section of FIG. 19 which also includes the electronics module. Section II of FIG. 20 is enlarged in FIGS. 21 and 22 to show the action of the spring member 1804 in greater detail. FIG. 21 illustrates the spring member 1804 in an uncompressed position. Alternatively, FIG. 22 illustrates the spring member 1804 in a compressed position which corresponds to the dispensing of medicine.

With reference to FIGS. 23–26, an enclosure 2300 of the docking station 300 is respectively shown in perspective, top, back, and side views. The enclosure 2300 includes a docking cradle 2304, an IR window 2308, a communication cable 2312, the second display 456, the menu buttons 460, a communication port 2500, a direct current power input 2504, and a reset button 2508. The docking cradle 2304 is shaped to receive the electronics module 116 in a such a way that the IR window 2308 is proximate to the IR transmitter and receiver 1512, 1516 on the electronics module 116. Behind the IR window 2308 is another IR transmitter and receiver which are used to couple the docketing station 300 to the electronics module 116. The display 456 presents information to the patient and the menu buttons 460 allow interaction with any displayed information. To allow serial communication with the user computer 304, the communication cable 2312 is plugged into the communication port 2500. The direct current power input 2504 receives power from an external transformer which is coupled to an alternating current wall outlet. In order to recover from firmware crashes in the controller 448, the reset button is able to reset the circuitry within the docking station 300.

Figure 27:
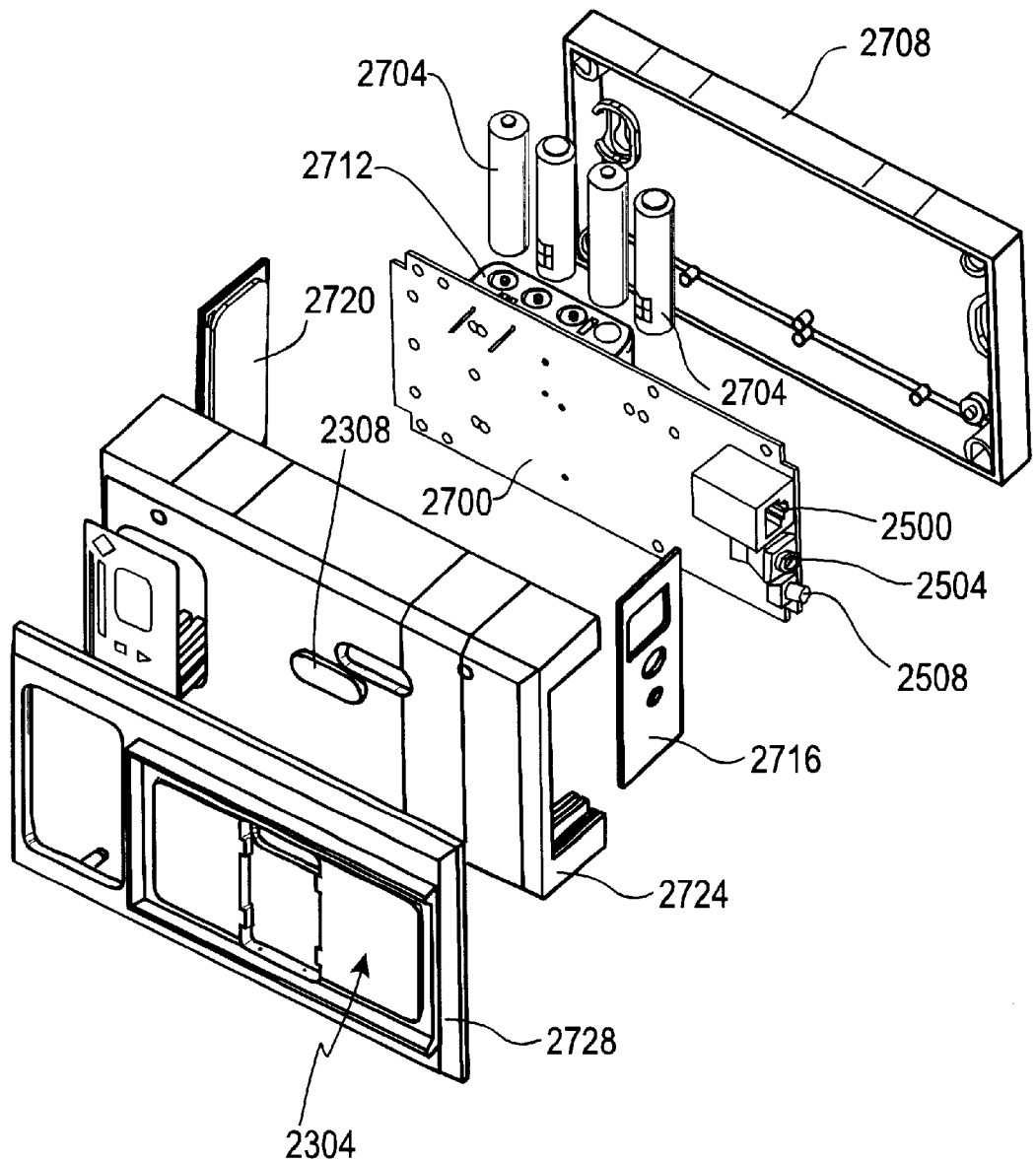
FIG. 27 is an exploded perspective view of the docking station of FIG. 23.

Referring next to FIG. 27, an exploded view of the docking station 300 is shown. The enclosure 2300 is comprised of a bottom 2708, top 2724, front panel 2720, back panel 2716 and guide plate 2728. Included within the enclosure are an electronics printed circuit board (PCB) 2700, batteries 2704 and a battery holder 2712. The electronics PCB 2700 includes the battery holder 2712, communication port 2500, direct current power input 2504, and reset button 2508 and further includes the circuitry for the communications port 452, second IR port 404, controller 448, and power supply 464. To provide redundant power, batteries 2704 may be inserted into a battery holder 2712. Battery power is used when there is no power applied to the direct current power input 2504.

With reference to FIG. 28, a hard-copy of a display from the practitioner's software is shown. The practitioner's software is updated with data from the medicine dispensing system 100. The data is updated by the patient management system 316 when the medicine dispensing system is docked. The data may be charted and otherwise analyzed with the practitioner's software. The medical practitioner can manage a number of patients with this software.

Additionally, the practitioner's software allows programming and reprogramming of the medicine dispensing system 100. The medicine type, number of doses, puffs per dose and timing of doses can be programmed into the medicine dispensing system 100 by the practitioner's software. Reminders can also be programed into the medicine dispensing system 100 which notify the patient when medication is needed by way of the speaker 444 or first display 440. Upon receiving a new medicine dispensing system 100, the patient docks the system 100 to have the programming performed. If the electronics module 116 is ever transferred to another medicine dispensing apparatus, the electronics module 116 is reprogrammed in a similar way.

Figure 29:
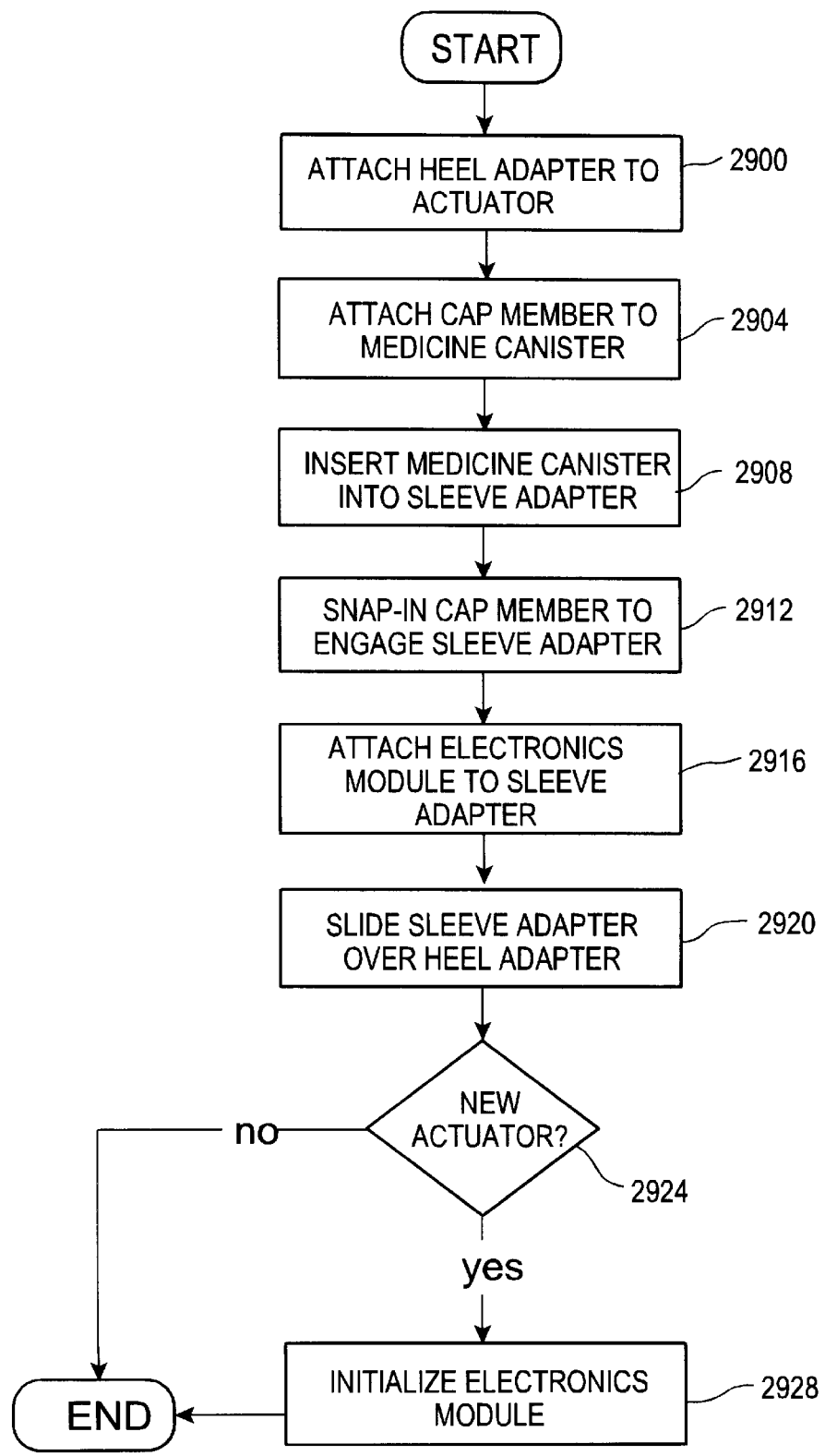
FIG. 29 is a flow diagram showing an embodiment of the steps for assembling and programming the medicine dispensing system.

Referring to FIG. 29, a flow diagram of the steps for assembling the medicine dispensing system 100 for one embodiment are shown. In step 2900, the heel adapter 108 is attached to the actuator 104. The vertical connectors 1300 snap around the bottom of the actuator 104 and the horizontal connectors 1400 snap around the front of the actuator 104. In step 2904, the cap member 120 is attached to the medicine canister 500. The double-sided tape 504 is used to affix the cap member 120 and medicine canister 500 together. In steps 2908 and 2912 the cap member 120 is affixed to the sleeve adapter 112. The medication canister 500 is inserted into the sleeve adapter 112 and the cap member is 120 snapped together with the sleeve adapter 112. In alternative embodiments, the cap member 120 could screw into with the sleeve adapter 112. In step 2916, the electronics module 116 is attached to the sleeve adapter 112. Connectors 516 retain the electronics module 116 to the sleeve adapter 112. After the assembly of the electronics module 116, cap member 120, medicine canister 500 and sleeve adapter 112 is complete, the sleeve adapter 124 is slid over the heel adapter 108 in step 2920 until the two snap together. The shape of the heel adapter 108 forces the window 512 of the sleeve adapter 124 to face forward. To view a medication label on the canister 500, the sleeve adapter 124 with attached cap member 120 and canister 500 are removed from the remainder of the medicine dispensing system 100. Then, the cap member 120 is turned to rotate the label on canister 500 into view through the window 512.

If the actuator 104 is new to the user, the electronics module 116 receives new programming. The actuator 104 could be entirely new to the patient and require programming, or the actuator 104 could merely be a change in medication and require reprogramming only. If the actuator 104 is the same or a replacement having the same configuration as the old actuator 104, no programming is required and the medicine dispensing system 100 is complete. A determination is made in step 2924 as to whether the actuator 104 is new to this patient and would need programming or reprogramming. In step 2928, programing or reprogramming of the electronics module 116 is performed by mating the medicine dispensing system 100 to the docking station 300, as described above.

Figure 30:
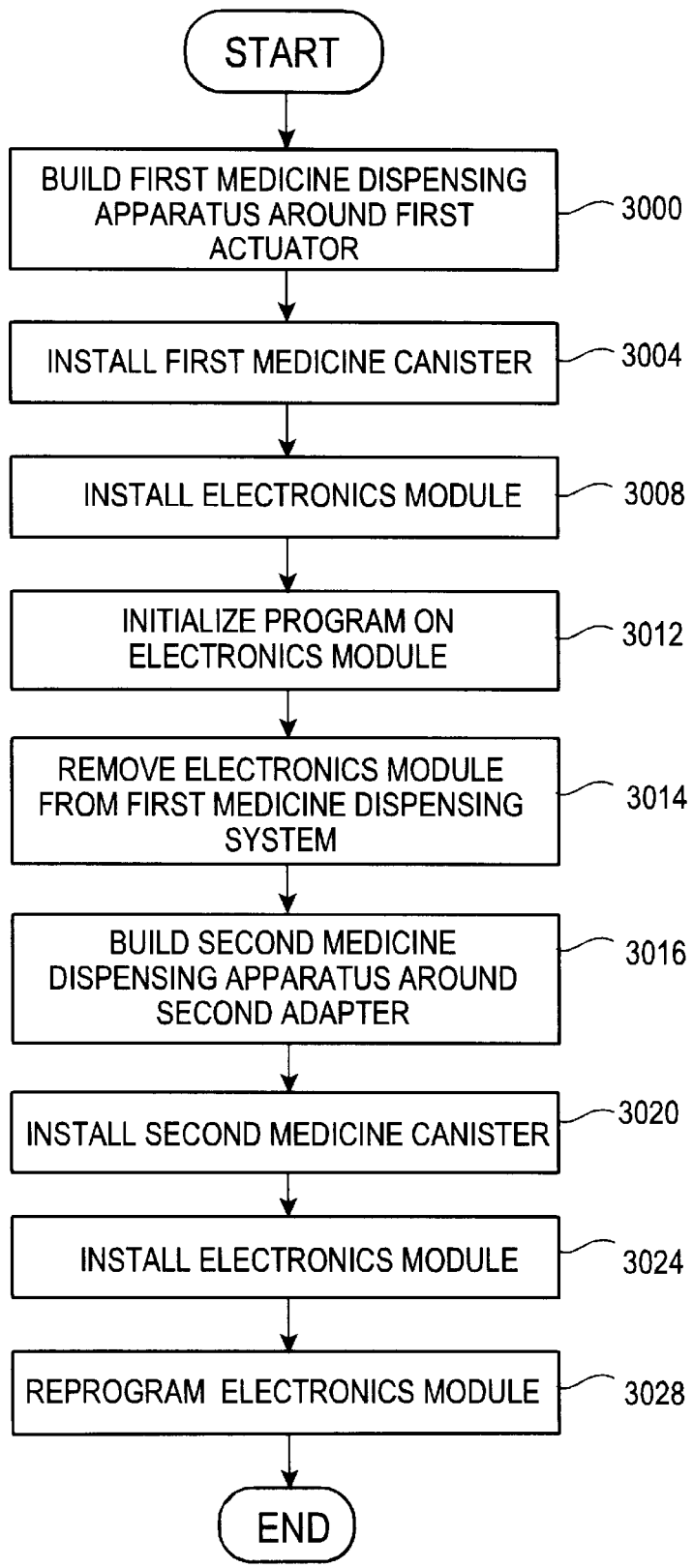
FIG. 30 is a flow diagram showing an embodiment of the steps for changing actuators.

With reference to FIG. 30, a flow diagram of the steps for changing to a different actuator 104 is shown. Changing to a different actuator 104 requires reprogramming the electronics module 116 accordingly for any new dosage regiment. In step 3000, the medicine dispensing apparatus is built. The first medicine canister is installed in step 3004. Next, the electronics module 116 is attached to the sleeve adapter 112 in step 3008. Once the building of the medicine dispensing system 100 is complete, the system is programmed the first time in step 3012. In between steps 3012 and 3014, a different medication and/or actuator 104 are provided to the patient. In step 3014, the electronics module 116 is salvaged from the first medicine dispensing system 100. Removal of the electronics module 116 typically damages the connectors 516 which retain the module 116. Accordingly, the damaged connectors render the sleeve adapter 112 unusable which is desirable for sanitation reasons. In steps 3016, 3020, and 3024, the second medicine dispensing apparatus is built. In this embodiment, the first medicine dispensing apparatus has a different mechanical configuration than the second medicine dispensing apparatus. Different heel and sleeve adapters 108, 112 are shaped to accommodate the different mechanical configuration. The heel and sleeve adapters 108, 112 from the first actuator have a geometric configuration which generally prevents them from being properly installed on the second actuator. The electronics module 116 is reprogrammed in step 3028 to accommodate the new dosage guidelines. In this way, a single electronics module 116 may be interchanged between a variety of actuators 104.

Figure 31:
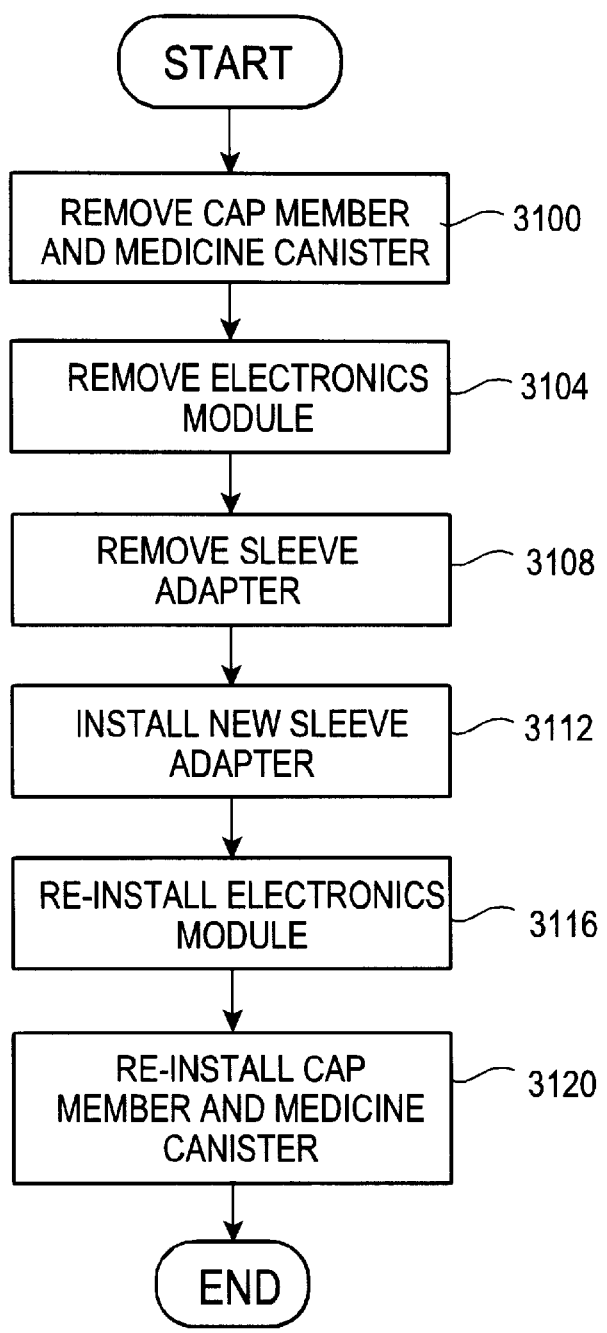
FIG. 31 is a flow diagram showing an embodiment of the steps for changing the battery for an embodiment of the medicine dispensing system.

Referring to FIG. 31, the steps for replacing the battery 412 for one embodiment is shown. In this embodiment, the battery 412 is integral to the sleeve adapter 112 so that the whole sleeve adapter 112 is disposed of to replace the battery 412. In steps 3100, 3104, and 3108, the cap member 120 and medicine canister 500, the electronics module 116 and sleeve adapter 112 are successively removed. A new sleeve adapter 112 with a new battery 412 is installed in step 3112. The electronics module 116 and cap member 120 and medicine canister 500 are reinstalled in steps 3116 and 3120 to complete the battery 412 replacement process. However, in embodiments where the cap member 120 snaps into the sleeve adapter 112, an assembly of the cap member 120, sleeve adapter 112 and medicine canister 500 are removed together in a single step.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. By way of example only, the invention need not be limited to dispensing liquid aerosol medications. Other applications can be implemented incorporating the principles of the present invention including dispensing dry powder medications. The embodiments discussed hereinabove are further intended to explain the best mode known of practicing the inventions and to enable others skilled in the art to utilize the inventions in such, or in other embodiments and with the various modifications required by their particular application or uses of the Inventions. It is intended that the appended claims be construed to include alternative embodiments to the extent permitted by the prior art.

What is claimed is:

1. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained, at least portions of said connector assembly move with the medicine canister when the medicine canister is moved to dispense medicine to the patient; and an electronics module on said connector assembly for obtaining the information related to patient usage of the medicine.

2. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained, said connector assembly including a sleeve adapter surrounding at least a majority of a perimeter of said actuator; and an electronics module on said connector assembly for obtaining the information related to patient usage of the medicine.

3. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained, said connector assembly including a heel adapter joined to said actuator and a sleeve adapter joined to said heel adapter and disposed outwardly thereof; and an electronics module on said connector assembly for obtaining the information related to patient usage of the medicine.

4. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained, said connector assembly including a cap member connected to a top of the medicine canister; and an electronics module on said connector assembly for obtaining the information related to patient usage of the medicine.

5. An adaptor assembly, as claimed in claim 4, wherein:

said connector assembly includes a sleeve adaptor and said cap member is connected to said sleeve adaptor.

6. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained; and an electronics module on said connector assembly for obtaining the information related to patient usage of the medicine, said electronics module including a switch element and said connector assembly including a heel adapter and in which said switch element is moveable relative to said heel adapter.

7. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained; and an electronics module for obtaining the information related to patient usage of the medicine, said electronics module being removable from said connector assembly and with at least portions of said connector assembly being disposable while said electronics module is reusable.

8. In a system for dispensing medication that includes a medicine canister that contains medicine to be dispensed, an actuator that houses the medicine canister, and an adapter assembly for obtaining information, said adapter assembly comprising:

a connector assembly connected to said actuator when information related to patient usage of the medicine in the medicine canister is being obtained, said connector assembly including a first sleeve adapter and a first heel adapter and in which said first sleeve adapter and said first heel adapter are connected to said actuator but each have a geometric configuration that prevents them from being properly connected to a second actuator; and an electronics module on said connector assembly for obtaining the information related to patient usage of the medicine.

9. A method for using the same electronics module with two different medicine dispensing apparatuses, comprising:

providing a first medicine dispensing apparatus including a first medicine canister containing a first medicine;

storing first information related to dispensing the first medicine with an electronics module joined to said first medicine dispensing apparatus;

providing a second medicine dispensing apparatus including a second medicine canister containing a second medicine; and storing second information related to dispensing the second medicine with said electronics module, with said electronics module being removed from said first medicine dispensing apparatus and joined to said second medicine dispensing apparatus.

10. A method, as claimed in claim 9, wherein:

said step of providing said second medicine dispensing apparatus includes rendering functionally inoperable connector portions of said first medicine dispensing apparatus with removal of said electronics module from remaining portions thereof.

11. A method, as claimed in claim 9, wherein:

said first medicine dispensing apparatus includes a first actuator and a first connector assembly for connection to said electronics module and in which said step of providing said second medicine dispensing apparatus includes replacing said first connector assembly with a second connector assembly that is compatible with a second actuator but is not compatible with said first actuator.

12. A method, as claimed in claim 9, wherein:

said step of storing said second information includes presenting an interface on a computer display screen for inserting information, said interface including identification information and a number of insertion sections for inserting information related to identification of the first medicine and dosages of the first medicine.

13. A method, a claimed in claim 12, wherein:

said number of insertion sections relate to a number of options in a group that includes: basic functions, time functions, device messages, patient information, and audio.

14. A method, as claimed in claim 12, wherein:

said step of storing said second information includes communicating said second information to said electronics module using a docking station.

* * * * *